(12) United States Patent
Suddaby

(10) Patent No.: US 6,328,738 B1
(45) Date of Patent: Dec. 11, 2001

(54) ANTERIOR CERVICAL FUSION COMPRESSION PLATE AND SCREW GUIDE

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 0 days.

(21) Appl. No.: 09/448,489

(22) Filed: Nov. 24, 1999

(51) Int. Cl.[7] .................................................. A61B 17/66
(52) U.S. Cl. .............................. 606/57; 606/61; 606/69
(58) Field of Search .................... 606/57, 60, 61, 606/69, 70, 71, 86, 90, 105, 58

(56) References Cited

U.S. PATENT DOCUMENTS

| | | | | |
|---|---|---|---|---|
| 1,025,008 | * | 4/1912 | Miner | 606/71 |
| 4,157,715 | * | 6/1979 | Westerhoff | 606/60 |
| 4,988,349 | * | 1/1991 | Pennig | 606/58 |
| 5,439,463 | * | 8/1995 | Lin | 606/61 |
| 5,601,551 | * | 2/1997 | Taylor et al. | 606/54 |
| 5,616,142 | * | 4/1997 | Yuan et al. | 606/61 |
| 5,672,177 | * | 9/1997 | Seldin | 606/71 |
| 5,720,746 | * | 2/1998 | Souberiran | 606/61 |
| 6,139,550 | * | 10/2000 | Michelson | 606/69 |
| 6,171,307 | * | 1/2001 | Orlich | 606/53 |

FOREIGN PATENT DOCUMENTS

9320771 * 10/1993 (WO) ...................................... 606/53

* cited by examiner

Primary Examiner—Jeffrey A. Smith
Assistant Examiner—Michael B. Priddy
(74) Attorney, Agent, or Firm—Shoemaker and Mattare

(57) ABSTRACT

An anterior cervical compression plate has a pair of slidable inserts, one situated in a recess at either end of the plate. The inserts, and the sides of the recesses, having meshing raked teeth which permit the inserts to move only toward one another. The inserts have openings which are placed over the heads of screws installed in the vertebrae, and maintain compression of bone grafts between the vertebrae. A special tool is also provided to aid the surgeon in installing in the vertebrae central screws which are engaged by the inserts.

7 Claims, 11 Drawing Sheets

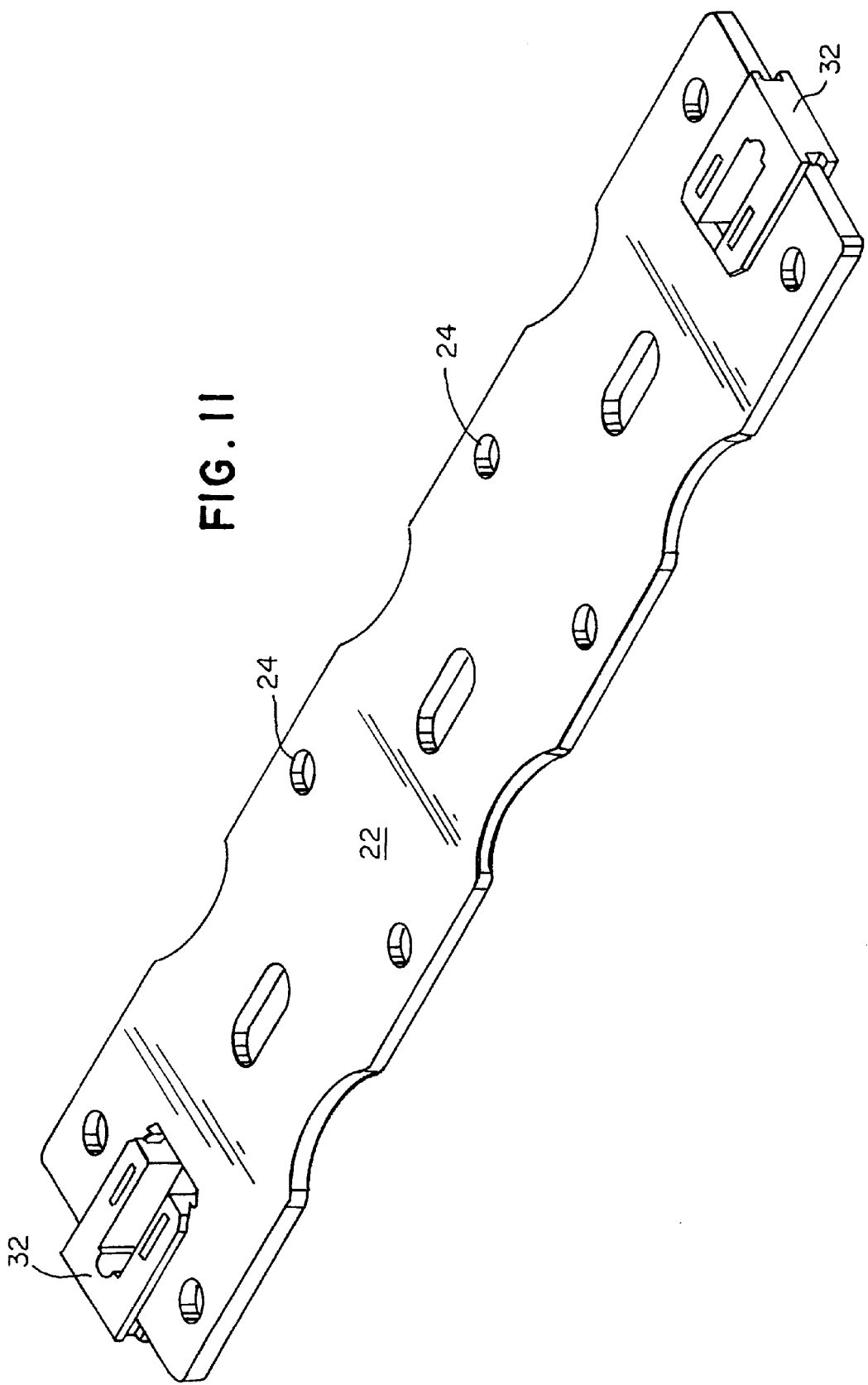

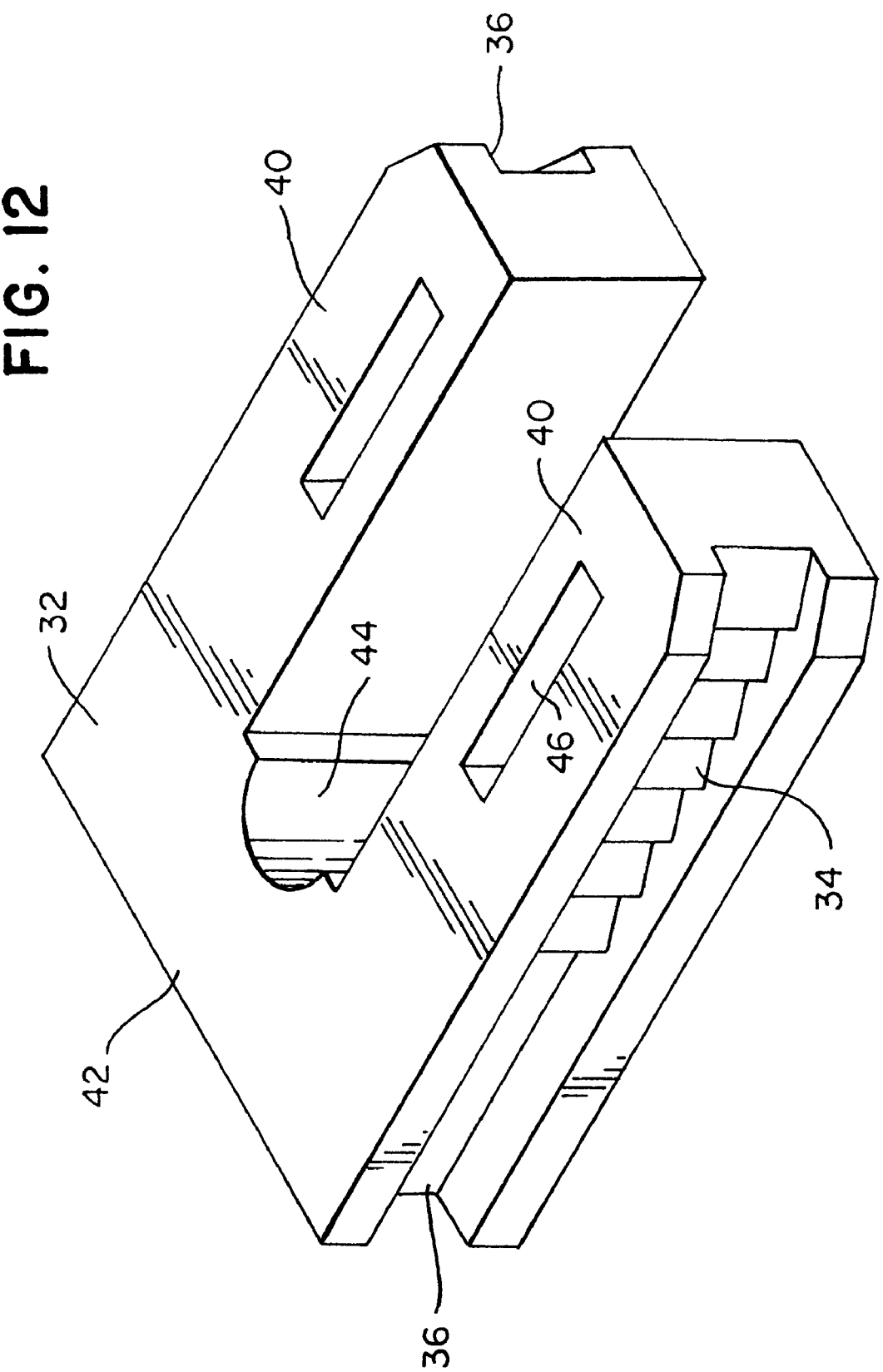

ANTERIOR CERVICAL FUSION COMPRESSION PLATE AND SCREW GUIDE

BACKGROUND OF THE INVENTION

This invention relates to orthopedic surgery, and more particularly to an anterior cervical fusion compression plate.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have the horizontal backbones of other animals. As a result, stresses acting upon the human backbone (or "vertebral column") are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvic or sacral region which are normally fused together and form the back part of the pelvis. This column of bones is critical for protecting the delicate spinal cord and nerves, and for providing structural support for the entire body.

Between the vertebral bones themselves exist soft tissue structures—discs—composed of fibrous tissue and cartilage which are compressible and act as shock absorbers for sudden downward forces on the upright column. The discs allow the bones to move independently of each other, as well. The repetitive forces which act on these intervertebral discs during repetitive day-to-day activities of bending, lifting and twisting cause them to break down or degenerate over time.

Presumably because of humans' upright posture, their intervertebral discs have a high propensity to degenerate. Overt trauma, or covert trauma occurring in the course of repetitive activities disproportionately affect the more highly mobile areas of the spine. Disruption of a disc's internal architecture leads to bulging, herniation or protrusion of pieces of the disc and eventual disc space collapse. Resulting mechanical and even chemical irritation of surrounding neural elements (spinal cord and nerves) cause pain, attended by varying degrees of disability. In addition, loss of disc space height reduces tension on the longitudinal spine ligaments, thereby contributing to spinal instabilites such as spinal curvature, and lithesis.

The time-honored method of addressing neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

In the cervical spine, the most common type of fusion utilizes either bone dowels (Cloward Technique) or bone blocks (Smith Robinson Technique). These procedures have been used now for over four decades. One of the main causes of failure of these fusion techniques is the failure to fuse, or non-union, at the site where the bone is grafted between the vertebral bodies. In an attempt to circumvent this problem, various plate-type mechanisms have been used both to provide immediate stability, and to reduce or eliminate movement at the site of the fusion to allow successful bone knitting, much as a cast on a fractured limb provides support until healing can occur.

It is recognized that for bone knitting to occur, the interfaces of bone required to knit or heal must be held in close apposition and motion between the knitting or fusion interfaces must be restricted sufficiently for a certain minimal time period to permit stable bone growth to occur.

To achieve these ends, prior inventors have developed a variety of both external braces and internal fixation instruments, some in the form of plates. Internal fixation is advantageous in that is obviates the need for cumbersome external braces, collars or supports and ensures essentially total compliance. U.S. Pats. No. 5,041,113, 5,234,431, 5,344,421, and 5,681,311 provide examples of prior vertebral bone plate systems. U.S. Pat. No. 3,604,414 discloses a plate for setting fractures, having separate elements which are attached to respective bone fragments and have a toothed interface to maintain the position of the fragments after they have been drawn together.

While interface apposition and retardation of motion are known to enhance bone healing, it is also recognized that if the bony surfaces to be fused are held together under a compression force, osseous union is further enhanced. While many plating systems maintain bony apposition and provide stability, few provide sufficient compression to be called compression plates, and none provide adjustable degrees of compression of the grafted bone.

SUMMARY OF THE INVENTION

It is an object of this invention to provide a cervical fusion compression plate that provides the desirable features of stabilizing grafted bone interfaces for sufficient time that bone union can occur. It is also the objective of this invention to provide adjustable degrees of compression of grated interfaces to further enhance the healing process and increase the probability of successful cervical bone graft fusion. It is also intended that this device be applicable to all generally accepted anterior cervical surgical approaches to the cervical spine, and that the device be sufficiently easy to apply such that is can be used readily even by surgeons with little experience with spinal instrumentation.

To achieve these objectives, a curved metal plate having roughly the curvature of a normal lordotic cervical spine is provided. At each end of the main body of the plate, there is a smaller U-shaped recess having a toothed surface at either side. Into this recess, a smaller, externally toothed secondary U-shaped insert is slid, so that the teeth mesh. The teeth are raked in opposition directions, as in a ratchet, so that relative motion can occur in only one direction (the compression direction), as long as the teeth are engaged. Incrementally increasing compression occurs as the plates are adjusted.

To facilitate placement of the fusion plate, a central screw is placed at the midline, below and parallel to the vertebral element's end face. This central screw is placed in each vertebral element above and below the fusion site. Placement of the central screw is aided by using a central screw guide which ensures that the screw is placed the correct distance from the end plate to avoid inadvertent placement of the screw in the disc space. The central screw guide has a needle-like probe which is pushed into the softer cervical disc material so that the exact location of the end plate can be determined. This allows placement of the central screw a predictable distance above or below a given vertebral end surface.

Once the central screws are placed, they can be utilized initially to distract the disc space to facilitate bone graft placement with any of the many available vertebral distraction instruments.

After the bone graft has been properly placed, the compression plate is then positioned so that the openings in the upper and lower U-shaped inserts fit over the upper central and lower central screws, respectively. Using a suitable pliers-like tool, the upper and lower U-shaped inserts are drawn toward the center of the plate. As the central screws are brought closer together, compression of the intervening bone graft results. Since the U-shaped inserts can move in only one direction with a ratcheting motion, gradually greater degrees of compression occur until optimal compression is deemed to have been achieved. The central screws are then tightened to firmly secure the entire plating system to the spine. Now, holes may be drilled for larger lateral screws, using holes in the plate as a template. The lateral screw holes are then tapped, and the lateral screws are inserted, permanently and more securely anchoring the bones to the plate.

An advantage of this system is that the central screw holes can be rapidly and accurately made with the aid of the central screw guide, which facilitates optimal central screw placement. Once they have been installed, the central screws may be used for distraction or compression: to facilitate surgical decompression of neural elements and placement of graft material, and thereafter for final optimal compression of implanted bone grafts.

It is anticipated that the surgeon will have on hand an assortment of compression plates of different lengths; an appropriate compression plate is selected, and is then simply placed over the central screws.

The small U-shaped inserts at the ends of the plate are then crimped so that the plate assembly itself serves to compress the bone grafts; a separate tool is not needed.

The central screws can then be simply tightened to provided additional stability, or they may be removed once the larger lateral screws are in place.

The central screws firmly and accurately hold the plate in position while drilling and tapping the holes for the lateral screws, thereby freeing up the surgeon's hand: he need not hold the plate in position while simultaneously drilling and tapping the bone.

By compressing bone with a ratchet-type mechanism, the surgeon has great flexibility in loading grafted bone with optimal compressive forces.

BRIEF DESCRIPTION OF THE DRAWINGS

In the accompanying drawings,

FIG. 11 is an isometric view of the compression plate, with two inserts installed, one at either end; and FIG. 12 is an isometric view of one of the inserts.

DESCRIPTION OF THE PREFERRED EMBODIMENT(S)

Figure 1:
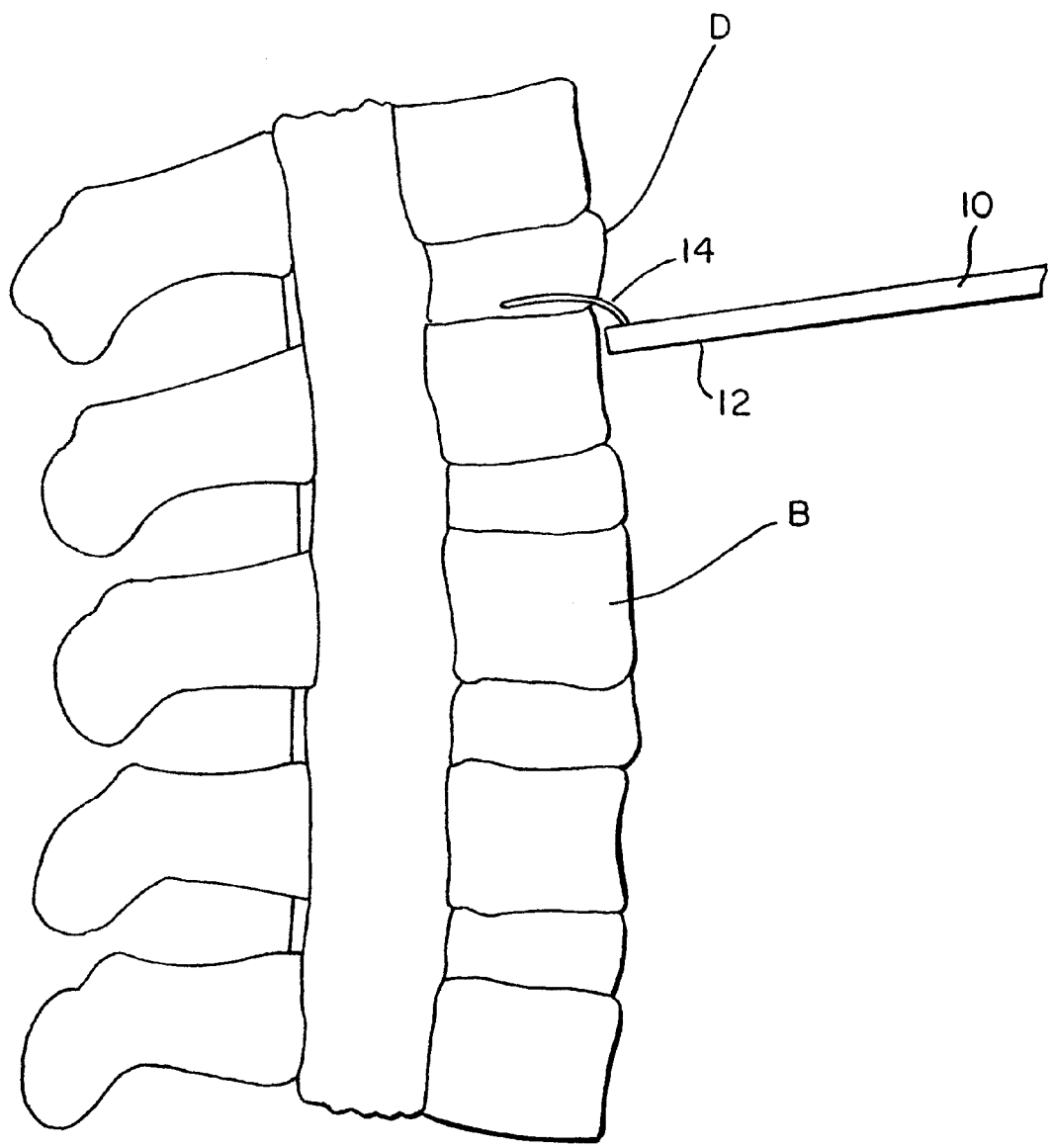
FIG. 1 is a lateral view of a cervical spine being prepared for drilling.

FIG. 1 shows a normal spine from one side. It comprises a series of vertebral bodies "B" separated by discs "D". The tool 10 which has been placed on the anterior side of the spine comprises a tube 12 and a needle-like probe 14 which is offset vertically from the axis of the tube 12. The amount of offset is such that, when the probe is inserted into one of the discs, the axis of the tube is more or less at the vertical mid-point of the adjoining vertebral element. It may be desirable to have on hand an assortment of such tools, with different offsets. A drill bit, now shown, is then passed through the tube, and a blind hole of a predetermined depth in drilled in each of the vertebrae above and below the fusion site.

Figure 2:
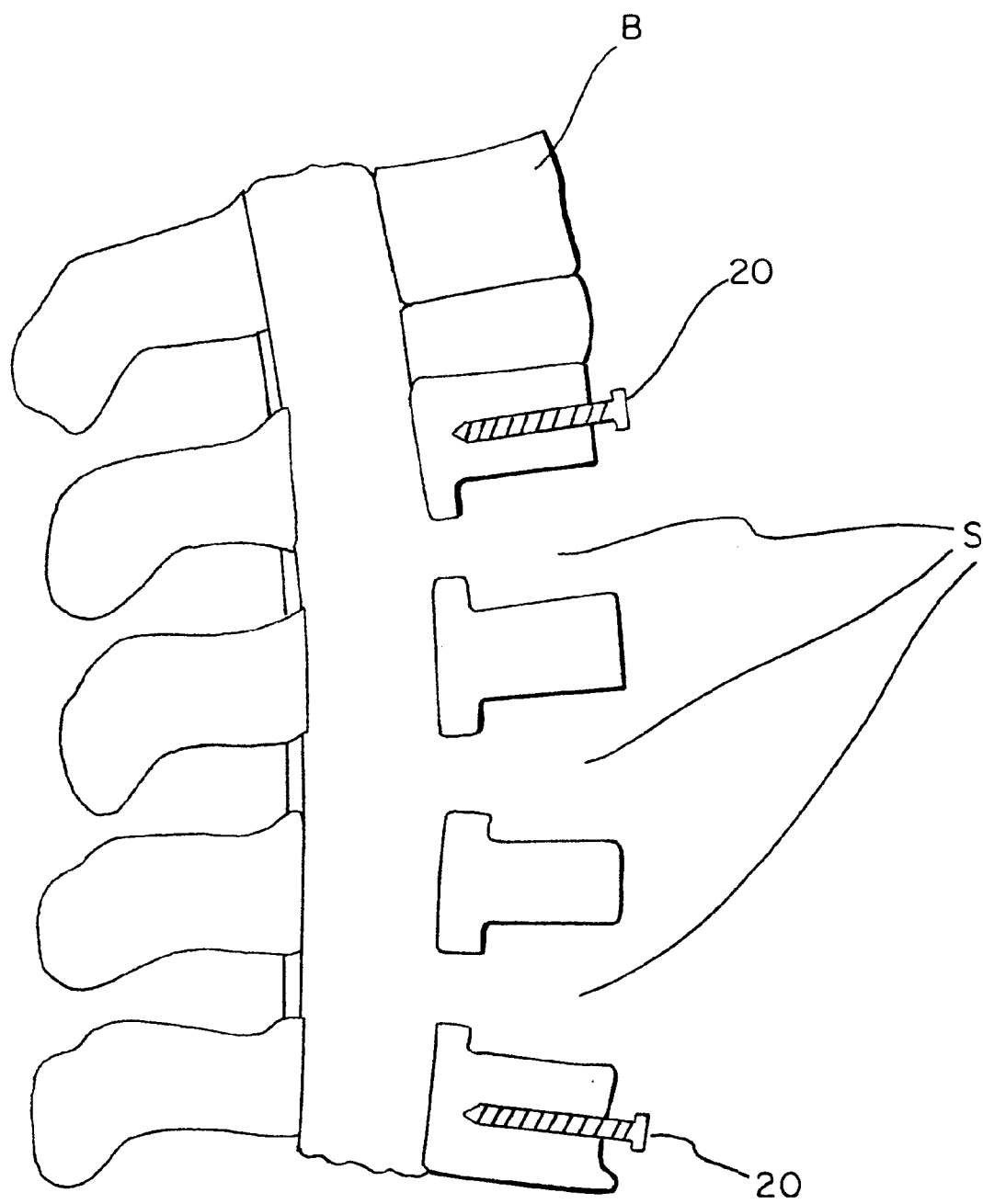
FIG. 2 is a view like FIG. 1, where three disc spaces have been prepared for grafting and a central screw has been placed in the bones above and below the graft site.
Figure 5:
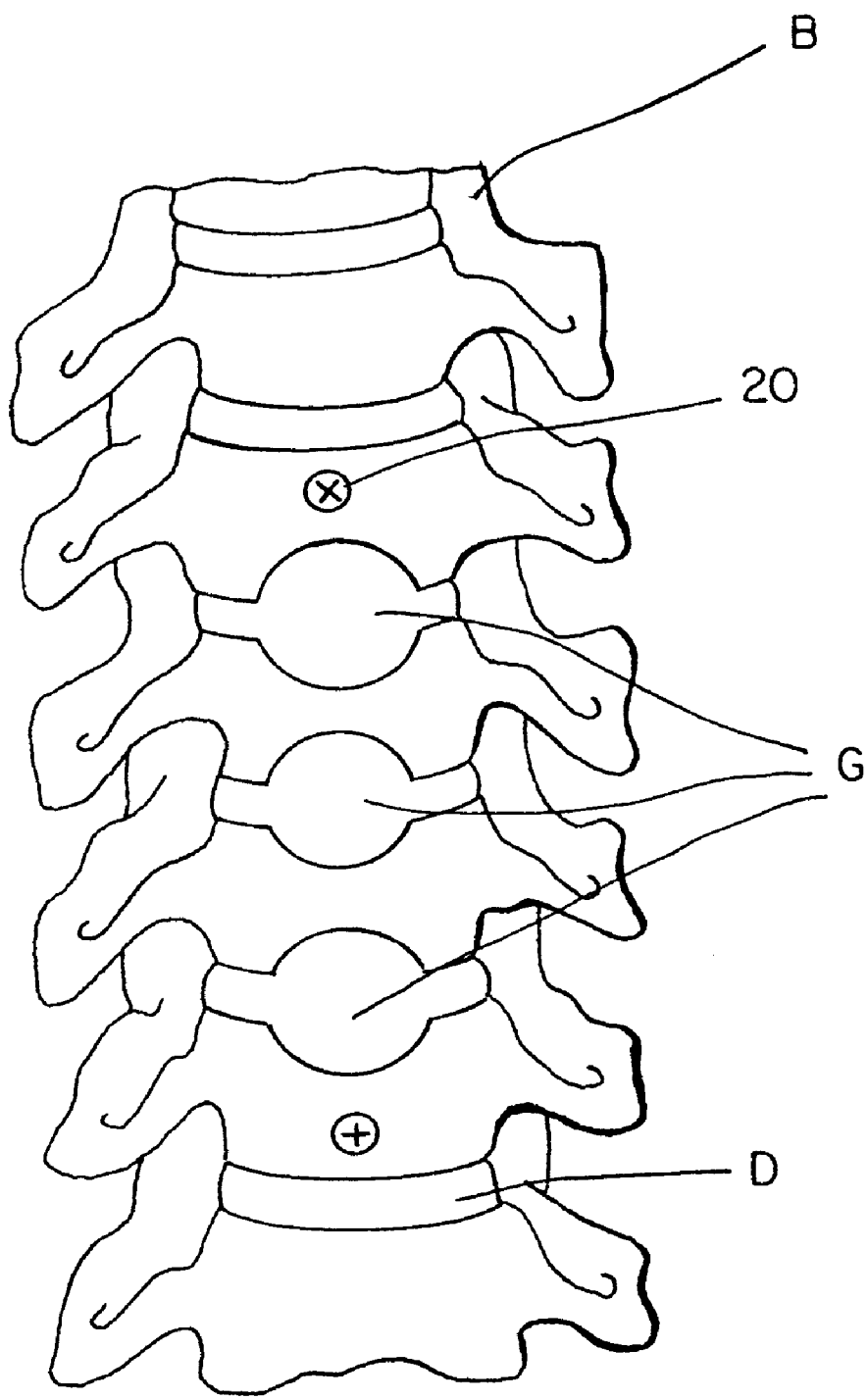
FIG. 5 is an anterior view of the spine, prepared as in FIG. 2.

In FIG. 2, some of the discs have been removed in preparation for spinal fusion. FIG. 5 shows how the space "S" has been enlarged by the surgeon, in the anterior view. One can see in either figure two central screws 20, which have been threaded into the holes previously drilled. The protruding heads of the central screws are convenient for manipulating the bones at this point, for example to distract them to enlarge the spaces into which bone grafts are to be placed.

Figure 3:
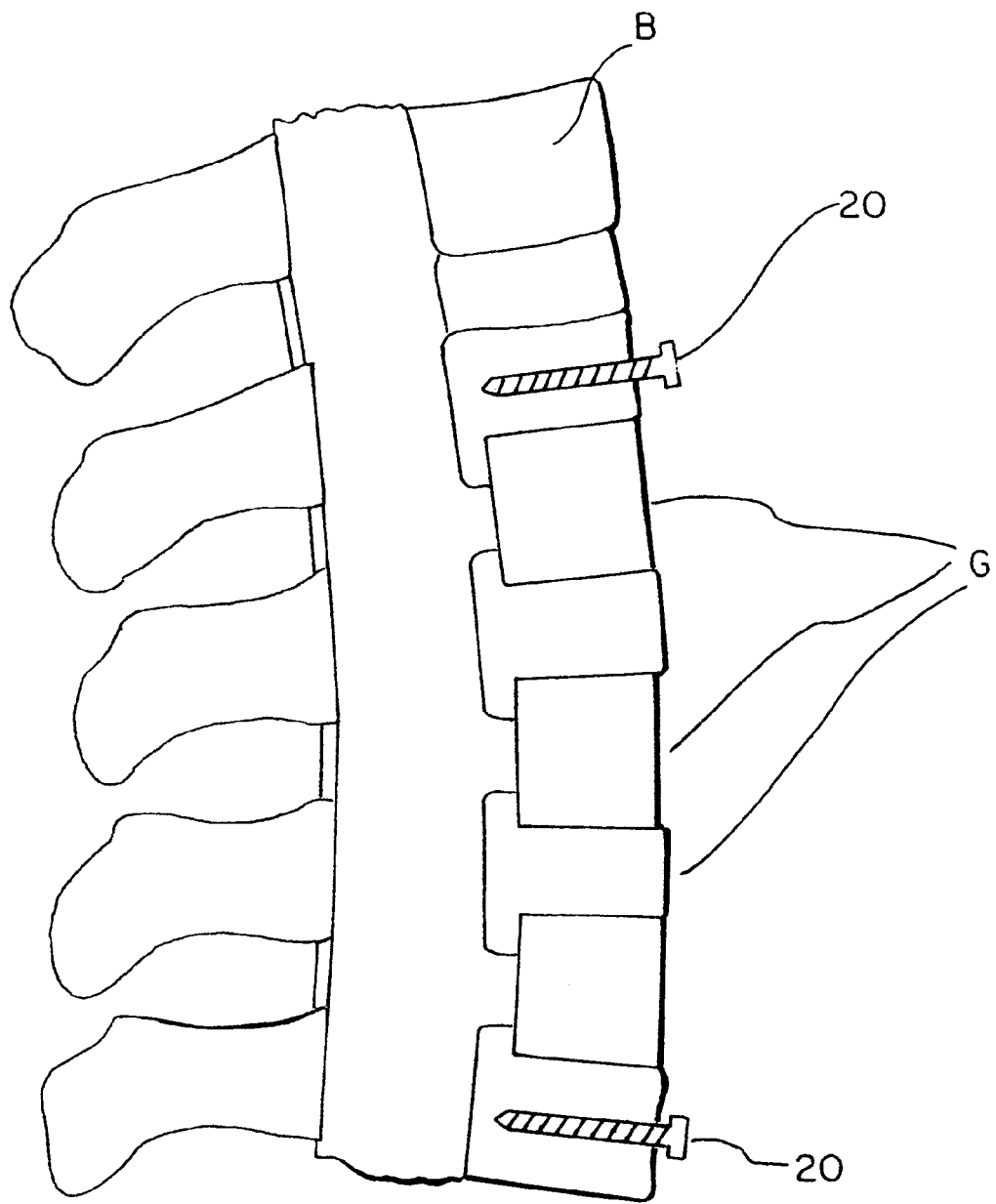
FIG. 3 is a view like FIG. 2, showing bone grafts which have been inserted in the disc spaces.
Figure 4:
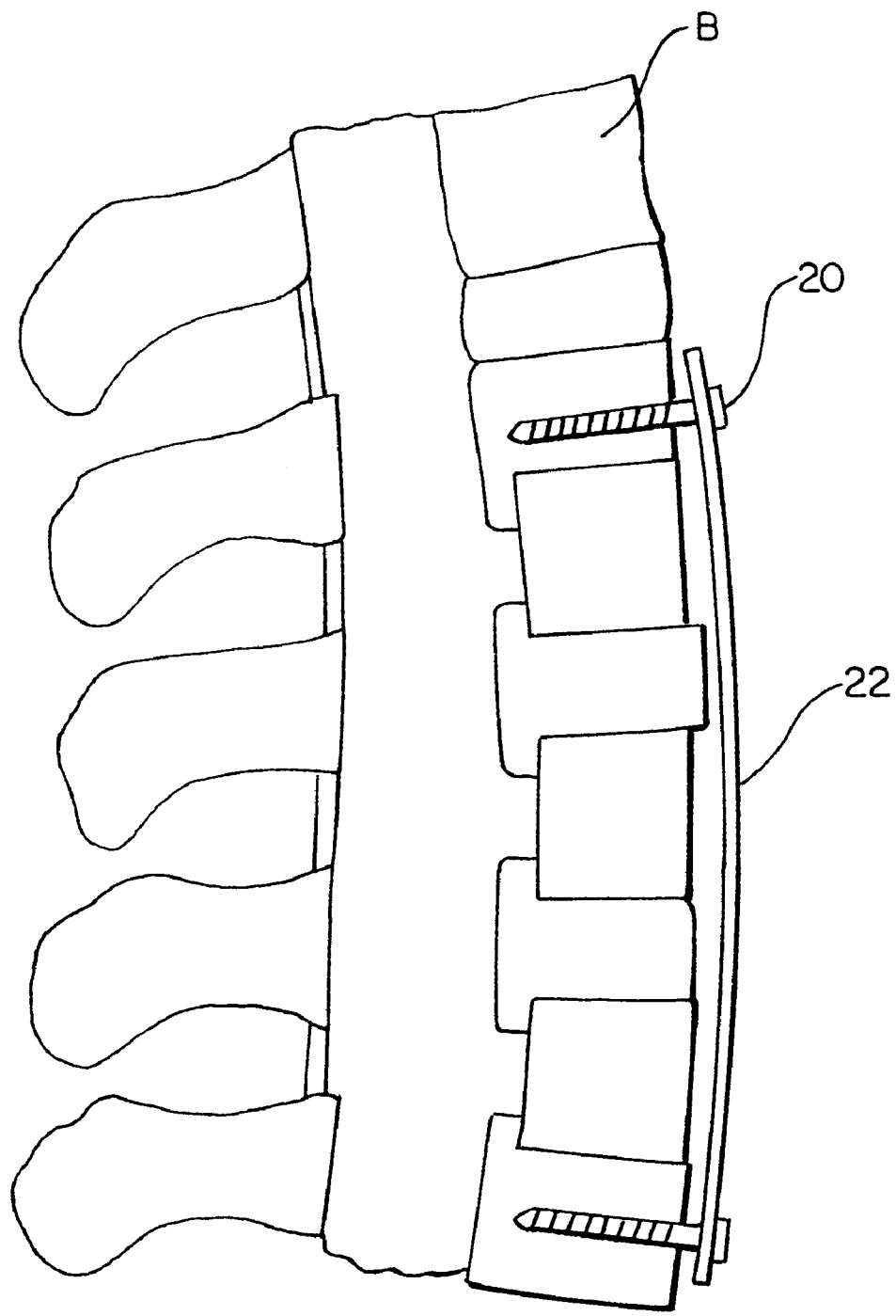
FIG. 4 illustrates a compression plate installed over the central screws.
Figure 6:
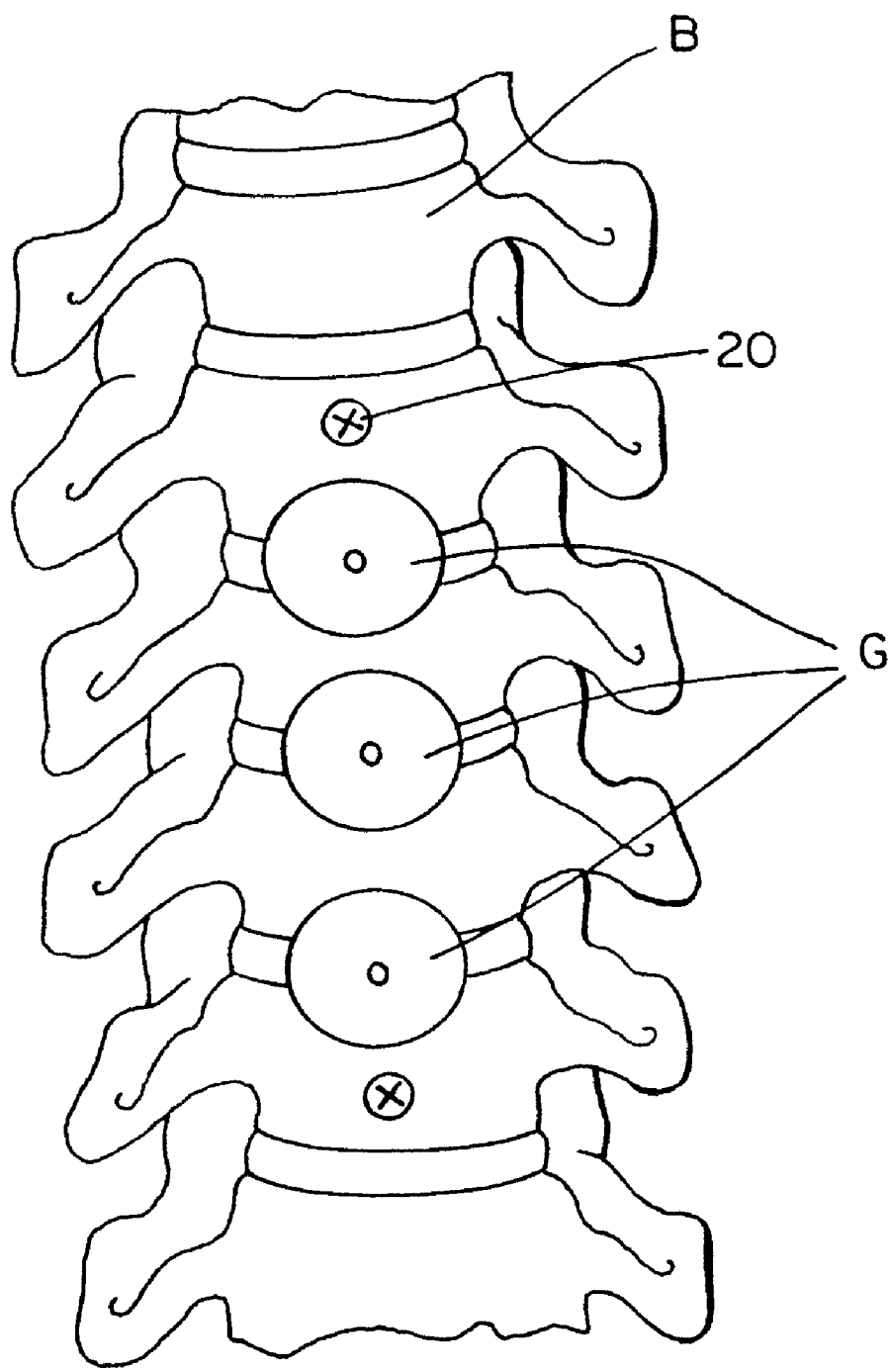
FIG. 6 is an anterior view, with grafts in place as in FIG. 3.
Figure 7:
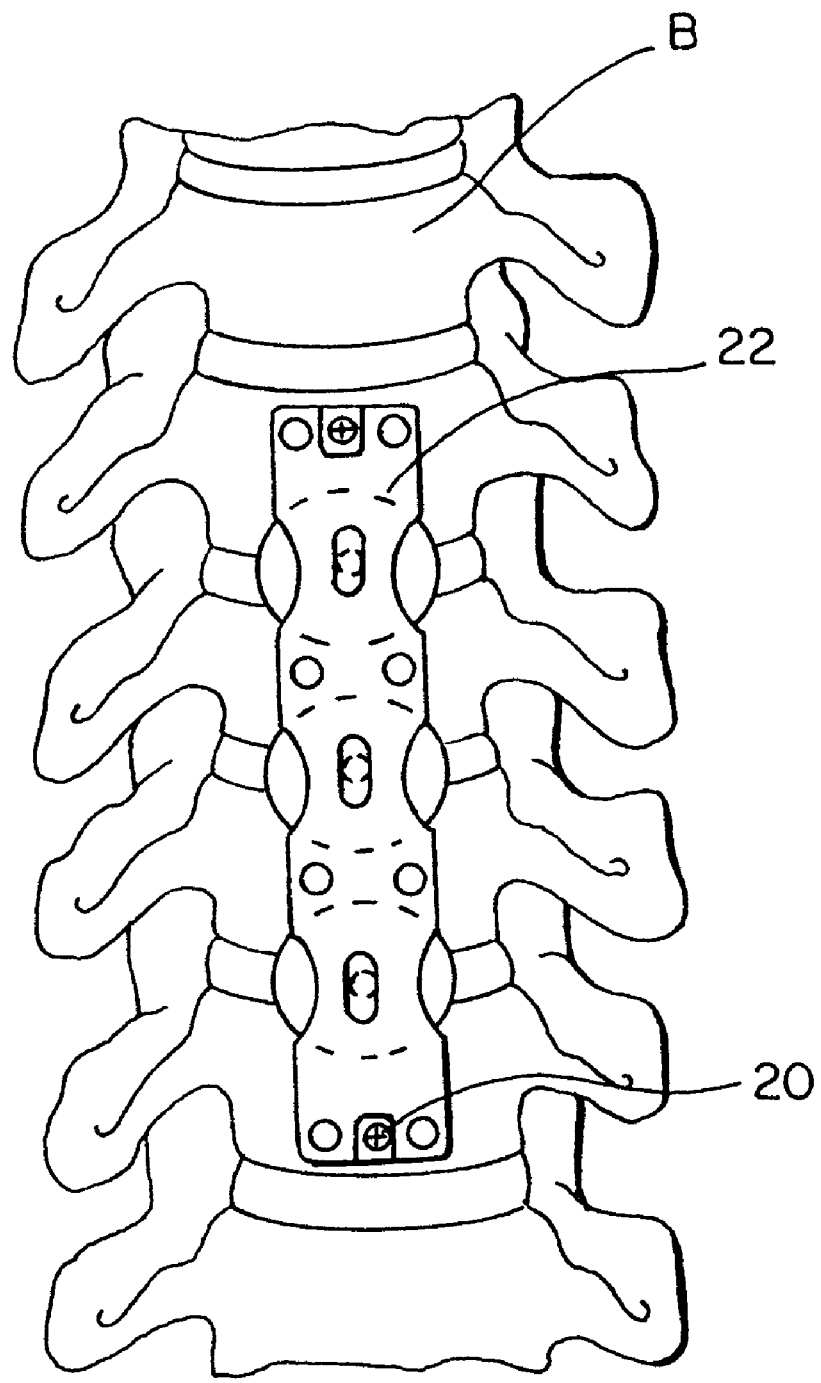
FIG. 7 is an anterior view, with a compression plate as in FIG. 4.
Figure 8:
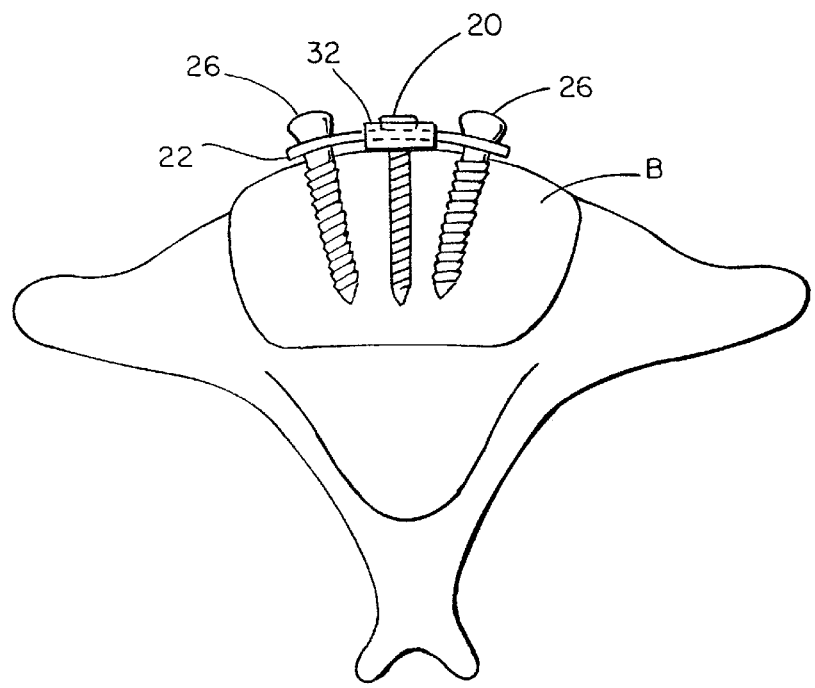
FIG. 8 is a sectional view, looking down the spine, showing the plate, one central screw, and a pair of lateral screws in addition.
Figure 9:
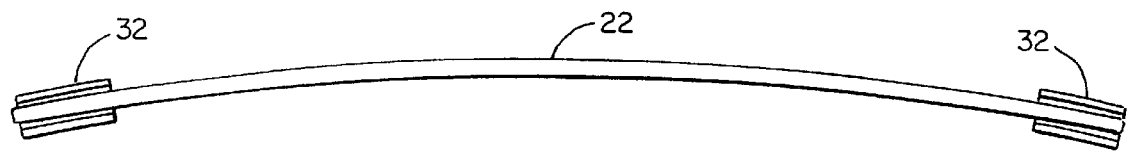
FIG. 9 is a side view of the compression plate, showing its curvature.

FIGS. 3 and 6 show the grafts "G" in place, and FIGS. 4 and 8 illustrate a compression plate 22 which has been placed over the screw heads. One may note the curvature of the plate (see also FIG. 9) matches that of the spine. Assorted plates may be provided with various curvatures to accommodate correspondingly different spinal curvatures.

Figure 10:
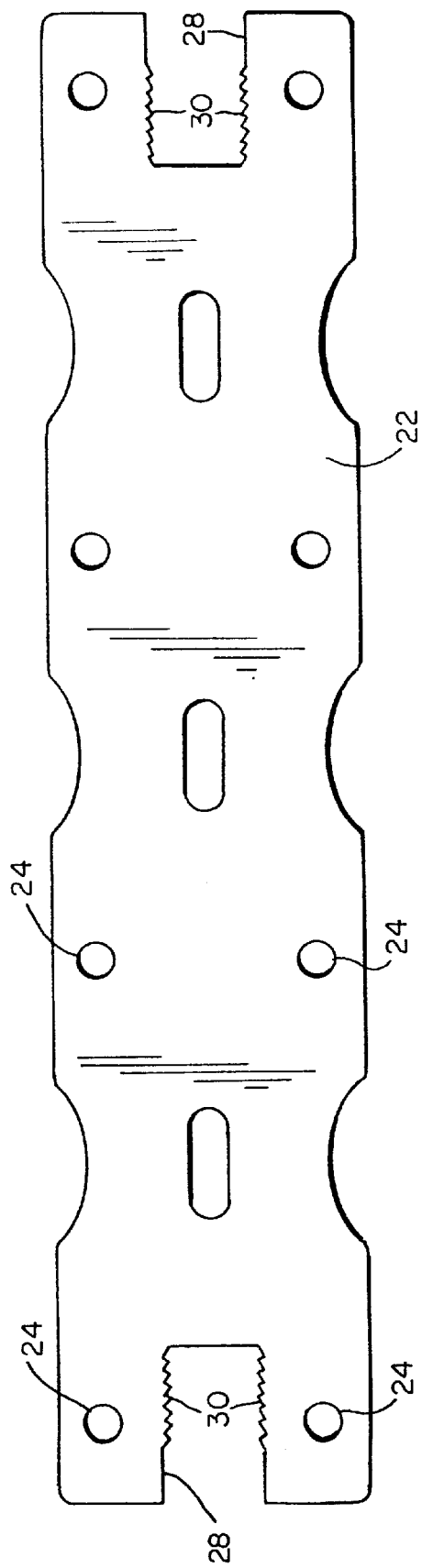
FIG. 10 is a front view of the compression plate.

FIG. 11 shows the plate assembly, comprising the plate 22 itself (FIG. 10), which has plural pairs of holes 24 for receiving the lateral screws 26 (FIG. 8). A rectangular recess 28 is formed at each end of the body, and the opposed edges of the recess are provided with a series of teeth 30. All these teeth are raked in a direction toward the opposite end of the body, as indicated by the arrow.

U-shaped inserts 32 are formed to seat in the recesses. Each insert (see FIG. 12) has two sets of external teeth 34, raked in a direction opposite to that of the teeth 30 on the sides of the recess 28, so that the teeth mesh when the inserts are pushed into the recess. Depending on the material of the insert, the teeth may be molded, stamped or machined. The grooves 36 at the edges of the inserts keep them seated in the recess, while permitting them to slide. The insert may be laminated from two or three separate elements, as shown in FIG. 12, by adhesives, soldering or welding. Alternatively, unitary construction may be possible. The choice of the method of manufacture would be a matter of ordinary skill. In any event, the resulting insert has grooves on either side which contain the teeth, and which retain the insert in the recess while allowing it to slide.

As shown in FIG. 12, each insert is somewhat U-shaped, having a pair of arms 40 extending from a bridging portion 42. The crotch 44 between the arms is sufficiently large that it can be placed over the head of one of the central screws so as to engage the screw shaft and maintain the compressive force on the spine during recovery.

It will be apparent that normally, because of the direction of rake of the teeth, the inserts will be able to move only towards one another, that is, in a direction drawing the bones together in compression. The rectangular apertures 46 in the arms provide a means by which one may release the ratchet teeth from engagement, should it ever be desired to retract or remove the inserts.

After the desired degree of compression has been attained, the surgeon drills holes in the vertebrae for the lateral screws, using the body as a template. After the lateral screws are driven into the vertebral elements, the central screws and the inserts may be removed, if desired.

It should be understood that, inasmuch as the invention is subject to variations and changes in detail, the above description and the drawings should be interpreted as only illustrative of the invention defined by the claims below.

I claim:

1. A cervical compression plate assembly having opposite ends for engaging screws extending from respective vertebral elements, said plate assembly comprising two ratcheting mechanisms, one at either of said opposite ends, for permitting the distance between the screws to be shortened, but preventing said distance from increasing, so as to maintain compression of bone graft material placed between the vertebral elements.

2. The invention of claim 1, wherein the plate has two recesses, one at either end of the plate, and further comprising a pair of inserts adapted for sliding movement within a respective one of said recesses lengthwise of said plate, said inserts and said recesses having teeth which interengage and permit relative movement in only one direction.

3. The invention of claim 2, wherein each of said recesses has opposed lateral sides with teeth formed thereon and each of said inserts has lateral edges provided with teeth for engaging the teeth of the sides of the recesses.

4. The invention of claim 3, wherein each insert has a pair of arms and a bridging portion extending between the arms, the insert being sufficiently resilient to permit the arms to deflect inwardly as the teeth ride over one another during compression of the plate assembly, while providing an outward bias to keep the teeth in engagement.

5. The invention of claim 4, wherein each of the arms has an aperture adapted to receive a respective jaw of a pliers-type tool when it is necessary to release the teeth from engagement.

6. The invention of claim 2, wherein both lateral edges of the insert have grooves for engaging the sides of the recess and keeping the insert within the recess.

7. The invention of claim 1, wherein the plate has plural pairs of apertures therein through which pairs of apertures lateral screws may be inserted into the vertebral elements to further stabilize the spine once proper compression has been achieved.

\* \* \* \* \*